US006992184B2

(12) United States Patent
Carina et al.

(10) Patent No.: US 6,992,184 B2
(45) Date of Patent: Jan. 31, 2006

(54) MACROCYCLIC TETRAAMIDO LIGANDS AS BLEACHING CATALYSTS AND SYNTHESIS THEREOF

(75) Inventors: Riccardo Filippo Carina, Geneva (CH); Carl Gibson, Merseyside (GB)

(73) Assignee: Carnegie Mellon University, Pittsburgh, PA (US)

( * ) Notice: Subject to any disclaimer, the term of this patent is extended or adjusted under 35 U.S.C. 154(b) by 148 days.

(21) Appl. No.: 10/362,088

(22) PCT Filed: Aug. 13, 2001

(86) PCT No.: PCT/EP01/09351

§ 371 (c)(1),
(2), (4) Date: Feb. 19, 2003

(87) PCT Pub. No.: WO02/16330

PCT Pub. Date: Feb. 28, 2002

(65) Prior Publication Data

US 2003/0168630 A1 Sep. 11, 2003

(30) Foreign Application Priority Data

Aug. 23, 2000 (GB) ............................................. 0020846

(51) Int. Cl.
*C07D 257/00* (2006.01)

(52) U.S. Cl. ...................... 540/460; 540/463; 510/311; 510/376

(58) Field of Classification Search ................. 540/460, 540/463; 510/311, 376
See application file for complete search history.

(56) References Cited

U.S. PATENT DOCUMENTS

| | | | |
|---|---|---|---|
| 4,517,122 | A | 5/1985 | Tomalia et al. |
| 4,577,042 | A | 3/1986 | Collins et al. |
| 4,758,682 | A | 7/1988 | Collins et al. |
| 5,189,160 | A | 2/1993 | Memeger, Jr. |
| 5,247,075 | A | 9/1993 | Parker et al. |
| 5,298,618 | A | 3/1994 | Speranza et al. |
| 5,445,755 | A | 8/1995 | Convents et al. |
| 5,474,576 | A | 12/1995 | Thoen et al. |
| 5,785,886 | A | 7/1998 | Kerschner et al. |
| 5,847,120 | A | 12/1998 | Collins et al. |
| 5,853,428 | A | 12/1998 | Collins et al. |
| 5,876,625 | A | 3/1999 | Collins et al. |
| 6,051,704 | A | 4/2000 | Gordon-Wylie et al. |
| 6,054,580 | A | 4/2000 | Collins et al. |
| 6,099,586 | A | 8/2000 | Collins et al. |
| 6,127,536 | A | 10/2000 | Deline et al. |
| 6,136,223 | A | 10/2000 | Collins et al. |
| 6,241,779 | B1 | 6/2001 | Collins et al. |
| 6,297,400 | B1 | 10/2001 | Deline et al. |
| 6,384,279 | B1 | 5/2002 | Deline et al. |

FOREIGN PATENT DOCUMENTS

| | | |
|---|---|---|
| WO | WO 94/12621 | 6/1994 |
| WO | WO 94/21777 | 9/1994 |
| WO | WO 95/31526 | 11/1995 |
| WO | WO 97/29174 | 8/1997 |
| WO | WO 97/48787 | 12/1997 |
| WO | WO 98/39405 | 9/1998 |

OTHER PUBLICATIONS

Al–Hassan. S. S. et al., Specific Inhibitors in Vitamin Biosynthesis. Part 7. Synthesis of Blocked 7,8–Dihydropteridines via α–Amino Ketones, J. Chem. Soc., Perkin Trans. 1 1985, pp. 1645–1659.
Bradshaw, J. S. et al., Aza–Crown Macrocycles, Chap IV, p. 146, John Wiley & Sons Inc. 1993.
Buschmann, J. et al., The Structures of Difluorodiisocyanatomethane, $CF_2(NCO)_2$:X–ray Crystallography, Gas Electron Diffraction, and Quantum Chemical Calculations, Phys. Chem. A 2000, 104, pp. 7123–7128.
Bushby, R. J. et al., The Introduction of Alkylidene Substituents into the 4–Position of the 3,3,5,5–Tetramethyl–Δ–pyrazoline Nucleus by the Thioketone plus Diazoalkane Reaction: Synthesis of Tetra substituted Episulphides and Alkenes, J. Chem. Soc., Perkin Trans. 1, pp. 2401–2408, 1979.
Collins. T. J., Designing Ligands for Oxidizing Complexes, Department of Chemistry, Carnegie Mellon University, Accounts of Chemical Research, 1994, 27, pp. 279–285.
Drake, N. L. et al. Synthetic Antimalarials. Some Derivatives of 8–Aminoquinoline, Laboratories of the University of Maryland, vol. 68, Aug. 1946, pp. 1536–1543.
Fletcher, G. A. et al., A List of Amino–Acids Derivatives Which Are Useful in Peptide Synthesis, Int J. Peptide Protein Res. 4, 1972, pp. 347–371.
Greene, T. W., Protactive Groups in Organic Synthesis, Chap. V, pp. 154–192, Chap. VII, pp. 218–287, Harvard University, John Wiley & Sons, 1981.
Kozmin, A. S. et al., Opening of the Three–Membered Ring of Derivatives of Cyclopropane–1, 1–Dicarboxylic Acid in the Reaction with Hydrazine Hydrate, trans. from Zhurnal Organicheskoi Khimil, vol. 7, No. 10, p. 2224, Oct, 1971, Journal of Organic Chemistry of U.S.S.R, pp. 2309–2310.
Kelnan, E. et al., Diiodosilane. 3. Direct Synthesis of Acyl Iodides from Carboxylic Acids, Esters, Lactones, Acyl Chlorides, and Anhydrides, J. Org. Chem. 1990, 55, pp. 3922–3926.
Krapcho, A. P. et al., α–Carbalkoxylations of Carboxylic Acids. A General Synthetic Route to Monoesters of Malonic Acids, Tetrahedron Letters No. 32, pp. 2721–2723, 1974.
Larock, R. C., Comprehensive Organic Transformations: A Guide to Functional Group Preparations, Wiley–VCH, New York. $2^{nd}$ ed., 1999, pp. 1941–1954.
Nakamura, M. et al., Fluorimetric Determination of Aromatuc Aldehydes With 4,6–Dimethoxyl–1,2–Diaminobenzene, Analytica Chimica Acta, 134, 1982, pp. 39–45.
Uffelman, E. S., Macrocyclic Tetraamido–N Ligands that Stabilize High Valent Complexes of Chromium, Manganese, Iron, Cobalt, Nickel and Copper, Chapter II, pp. 39–97, California Institute of Technology, Aug. 19, 1991.

Primary Examiner—Gregory R. Del Cotto
(74) Attorney, Agent, or Firm—Kirkpatrick & Lockhart LLP

(57) ABSTRACT

The invention relates to a novel synthetic route for a group of ligands and to an improved catalyst containing the ligand. The invention also provides use of a ligand for inhibiting dye transfer.

11 Claims, No Drawings

MACROCYCLIC TETRAAMIDO LIGANDS AS BLEACHING CATALYSTS AND SYNTHESIS THEREOF

FIELD OF THE INVENTION

The present invention relates to the synthesis and use of macrocyclic metal-ligand complexes as bleaching catalysts. In particular it relates to a novel synthetic route for a group of these ligands and to an improved catalyst containing the ligand.

BACKGROUND OF THE INVENTION

Oxidation catalysts comprising metal-complexes are well known. One class being macrocyclic ligands, which co-ordinate with a transition metal ion. Such catalysts have been used in laundry compositions as parts of a bleaching system. These catalysts activate $H_2O_2$ or other peroxygen sources in water, and are effective at neutral to basic pH.

A catalyst is disclosed in WO 98/03263, filed Jul. 21, 1997, (Collins), which comprises a macrocyclic (tetra) amido N-donor. The macrocycle is capable of complexing with a metal ion, for example an iron III or IV. The complex also comprises axial ligands, for example as chloride or water, and one or more counter ions, for example tetraphenylphosphonium and tetraethylammonium.

U.S. Pat. No. 5,853,428, filed Feb. 24, 1997, (Collins) discloses use of similar catalysts in laundry detergent compositions.

Bleaching catalysts are of particular utility in the prevention of so-called 'dye transfer'. This occurs when dyestuffs are released from one region of a cloth article during laundering and later re-adsorbed at another location or on another article. It is advantageous to bleach the dyestuff while it is in aqueous solution, thereby preventing or reducing its transfer.

For reasons of toxicological and environmental acceptance, it is preferable that the axial ligands and counter-ions are relatively benign. Ions such as trifluoroacetate, tetra-phenylphosphonium and tetra-ethylammonium are not preferred where they would typically come into skin-contact as a consequence of use.

Several synthetic routes are known for the preparation of the catalysts described in the 'Collins' patents. In one such route, described in U.S. Pat. No. 6,051,704, Filed Jul. 22, 1996, an alpha or beta amino carboxylic acid, for example a alpha-amino isobutyric acid, is reacted with an activated malonate or oxalate derivative, for example a di-methyl malonyl chloride, with mild heating. Upon completion of a double coupling reaction, hydrolysis of the product yields a diamine-containing intermediate, a macro linker. In a further step, a diamine, typically an ortho-phenylene diamine, is reacted with the macro linker in the presence of a coupling agent to form a tetra-amido macrocycle. The macrocycle is subsequently complexed with a metal in the presence of appropriate ligands.

The synthetic route described in the 'Collins' patents is believed to produce a relatively low yield of a relatively impure material, and is believed unsuitable for large scale use.

An azide based synthetic route to macrocyclic tetra-amido ligands is described in Uffelman, E. S., PhD Thesis (California Institute of Technology, [1992]). This is described in further detail in U.S. Pat. No. 5,853,428, filed Feb. 24, 1997.

A further synthetic route is disclosed in U.S. Pat. No. 6,127,536 (Deline et al., filed May 25, 1999, issued Oct. 3, 2000). In this synthesis 1,2-phenylenediamine is reacted with 2-bromoisobutyryl bromide to form a precipitating intermediate which is cyclised by reaction with diethyl malonyl dichloride.

SUMMARY OF THE INVENTION

We have determined how an alternative synthetic route can be applied to obtain an improved yield of a ligand, which is believed to contain low levels of impurities. Furthermore, this yield and purity enables the formation of complexes in which the axial ligand is chlorine or water.

In simple terms, this route employs an N-protected amino acid, which is first reacted, at its carbonyl end, in the form of an acid chloride, with a diamine and subsequently deprotected to produce a macro-linker with available amino groups. This macro-linker is reacted with a di-carbonyl species to form the macrocycle. This differs from the prior route in which the macro-linker is formed by reaction at the amino group of the acid and subsequent ring closure occurs across the carbonyl groups of the amino acid residue.

Accordingly, a first aspect of the present invention provides a method for the synthesis of a ligand having the structure:

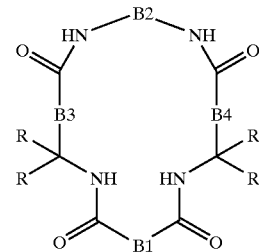

wherein:
$B_1$, $B_3$ and $B_4$ each represent a bridging group having zero, one two or three carbon containing nodes for substitution, and $B_2$ represents a bridging group having at least one carbon containing node for substitution, each said node containing a C(R), C($R_1$) ($R_2$) or C($R_2$)$_2$,
each R substituent is the same is the same or different from the remaining R substituents and
  (i) is selected from the group consisting of alkyl, alkenyl, cycloalkyl, cycloalkenyl, aryl, alkynyl, alkylaryl, halogen, alkoxy, phenoxy and combinations thereof, or
  (ii) form a substituted or unsubstituted benzene ring of which two carbons on the ring form nodes in the B-unit,
said method comprising the steps listed below in the order given
  a) protecting the amino group of an amino acid comprising HOOC—$B_3$—CRR—$NH_2$ and/or HOOC—$B_4$—CRR—$NH_2$,
  b) activating the carbonyl group of said amino acid,
  c) reacting the carbonyl-activated amino acid with a diamine $H_2N$—$B_2$—$NH_2$ to form a diamide diamine,
  d) deprotecting said protected amino groups, and,
  e) reacting the de-protected diamide diamine with an activated di-carbonyl compound to form a tetra-amine macrocycle.

It is preferred that HOOC—$B_3$—CRR—$NH_2$ and HOOC—$B_4$—CRR—$NH_2$ in step a) are the same.

The aforementioned synthetic method is not restricted to $B_1$, $B_2$, $B_3$ and $B_4$ as defined above. One skilled in the art will appreciate the $B_1$, $B_2$, $B_3$ and $B_4$ may represent any suitable spacing group that does not prevent the synthetic method from proceeding. Where required a group that does inhibit the reaction is protected. The particular length $B_1$, $B_2$, $B_3$ and $B_4$ may effect the reaction because of entropy factors; nevertheless one skilled in the art will appreciate the limits in size of any ring being formed. It is with the scope of the present reaction for a chelating ion to be used to aid cyclization.

A further aspect of the present invention subsists in those complexes, which have simple axial ligands (water or halide) and a simple counter-ion (such as lithium). It is believed that these ligands are environmentally and toxicologically more acceptable than ligands such as trifluoroacetate, tetra-phenylphosphonium and tetra-ethylammonium.

Accordingly, a further aspect of the present invention provides a bleach activator having the structure:

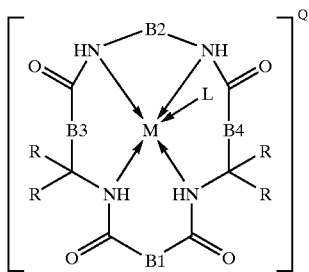

wherein:

$B_1$, $B_3$ and $B_4$ each represent a bridging group having zero, one two or three carbon containing nodes for substitution, and $B_2$ represents a bridging group having at least one carbon containing node for substitution, each said node containing a C(R), C(R$_1$)(R$_2$) or C(R)$_2$, each R substituent is the same is the same or different from the remaining R substituents, and
  (i) is selected from the group consisting of alkyl, alkenyl, cycloalkyl, cycloalkenyl, aryl, alkynyl, alkylaryl, halogen, alkoxy, phenoxy and combinations thereof, or
  (ii) form a substituted or unsubstituted benzene ring of which two carbons on the ring form nodes in the B-unit;

M is a transition metal ion;

L is an axial ligand selected from the group consisting of water and halide; and, Q is an alkali metal counter-ion.

It is also within the scope of the present invention to have a bleach activator, wherein M is selected from the group consisting of Fe, Mn, Cr, Cu, Co, Ni, Mo, V, Zn and W.

The present invention also extends to a packaged composition comprising a bleach activator as defined together with instructions for its use in a method of laundering fabrics.

DETAILED DESCRIPTION OF THE INVENTION

Throughout the description and claims generic groups are used, for example alkyl, alkoxy, aryl etc. Unless otherwise specified the following are preferred group restrictions that may be applied to generic groups found within compounds disclosed herein. Alkyl: linear and branched C1–C8-alkyl; alkenyl: C2–C8-alkenyl, cycloalkyl: C3–C8-cycloalkyl; cycloalkenyl: C4–12-cycloalkenyl having a single cyclic ring or multiple condensed rings and at least one point of internal unsaturation which can be optionally substituted with from 1 to 3 C1–C8-alkyl groups; aryl: selected from homoaromatic compounds having a molecular weight under 300, alkynyl: C2–C12-alkynyl; alkylaryl: C1–12-alkylaryl, wherein the aryl selected from homoaromatic compounds having a molecular weight under 300; halogen: selected from the group consisting of: F; Cl; Br and I; and, alkoxy: C1–C6-alkoxy.

Unless otherwise specified the following are more preferred group restrictions that may be applied to groups found within compounds disclosed herein. Alkyl: linear and branched C1–C6-alkyl; alkenyl: C3–C6-alkenyl; cycloalkyl: C6–C8-cycloalkyl; cycloalkenyl: C4–8-cycloalkenyl having a single cyclic ring or multiple condensed rings and at least one point of internal unsaturation which can be optionally substituted with from 1 to 3 C1–C8-alkyl groups; aryl: selected from group consisting of: phenyl; biphenyl; naphthalenyl; anthracenyl; and phenanthrenyl; alkynyl: C2–C8-alkynyl, alkylaryl: C1–6-alkylaryl, wherein the aryl is selected from selected from group consisting of: phenyl; biphenyl; naphthalenyl; anthracenyl; and phenanthrenyl; halogen: selected from the group consisting of: F and Cl; and, alkoxy: C1–C4-alkoxy.

Preferred compounds of the present invention have R=methyl. B3 and B4 are preferably absent, the two related sides of the ring being derived from a 'classical' amino acid in which the amino group is located on the alpha-carbon. A preferred starting amino acid is 2-amino iso-butyric acid. ($H_2N$—C($CH_3$)$_2$—COOH).

In the initial stage of the synthesis, the amino group of the acid is protected. The choice of protecting groups during synthesis to prevent undesirable reactions will be evident to one skilled in the art. For a discussion of protecting groups in organic synthesis the reader is directed to T. W. Green and P. G. M. Wuts, Protective Groups In Organic Synthesis 2nd Ed.; J. Wiley and Sons, 1991. Phthalic anhydride has been found to be a suitable protecting agent.

Activation of the carbonyl group following protection can be achieved by several means. One suitable means is reaction with a thionyl halide to yield the acyl halide. Reaction with an excess of thionyl chloride is preferred.

Following activation of the carbonyl, the protected macro-linker is formed by reaction with a diamine. The preferred diamines are phenylenediamines, preferably the o-phenylenediamine. These may be optionally substituted as described in the patents of Collins et al., as mentioned above. It is preferred to use the unsubstituted diamine.

The protected amino groups of the macro-linker may be unprotected by any suitable reaction. Where phthalic anhydride has been used as the protecting agent the de-protection can conveniently be accomplished through treatment with hydrazine hydrate.

Ring closure is conveniently obtained through reaction of the macro-linker with a di-carbonyl species, which has been activated. Preferably, B1 comprises a single substituted carbon atom. It is preferred that the portion of the heterocycle ring comprising B1 is derived from a malonate or oxalate. B1 most preferably is —(Me)$_2$C—. Dimethylmalonyl chloride is a suitable reagent. It is preferable that the ring closure reaction is performed slowly and at high dilution to prevent the formation of side products.

The following schematic shows a reaction scheme for the synthesis of a compound according to a preferred embodiment of the present invention. The individual reactions are described in more detail below. The amino acid, 2-aminoisobutyric acid, 'A', is reacted with a protecting agent to form a derivative with a protected amino group 'B'. The carbonyl group of the protected amino acid is then activated to form species 'C'. Reaction of two moles of 'C' with a mole of o-phenylene diamine yields the derivative 'D', which is subsequently deprotected at '1' to give the macro-linker 'E'. One skilled in the art will understand that differing protective groups may be used in the reaction, nevertheless a use of a single type of protecting group is preferred. Species 'E' is reacted with dimethyl malonyl chloride to close the ring structure and produce the final ligand (not shown). Metallisation of the ligand gives the active catalyst.

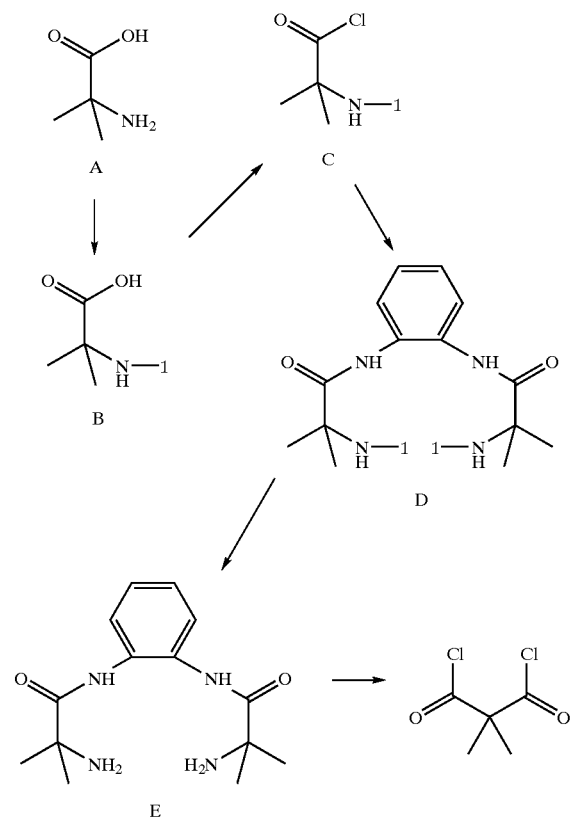

Metallation of the ligand is preferably performed under nitrogen and in a non-aqueous solution such as dry tetrahydrofuran (THF). The transition metal is preferably selected from groups VI, VII, VIII, IX, X and XI of the periodic table. More preferably the metal is selected from the group consisting of Fe, Mn, Cr, Cu, Co, Ni, Mo, V, Zn and W. Particularly preferably the metal is selected from the group comprising: Fe, Mn, Cu and Co. Iron is the most preferred metal.

Suitable counter ions are K, Li or Na, most preferably lithium.

The most preferred compound is that in which the ligand is 5,6-benzo-3,8,11,13-tetraoxo-2,2,9,9,12,12-hexamethyl-1,4,7,10-tetraazacyclotridecane as shown below as the Fe form, the axial ligand 'L' is water or preferably chloride. The counter-ion 'Q' is preferably lithium. This can also be described as 3,4,8,9-tetrahydro-3,3,6,6,9,9-hexamethyl-1H-1,4,8,11-benzotetraazocyclotridecane-2,5,7,10 (6H, 11H) tetrone.

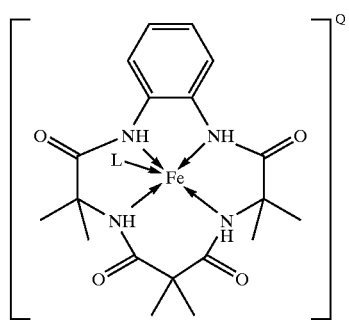

The present invention also extends to fully formulated products containing the catalysts disclosed herein. Such products will generally contain a detergent active and will typically contain one or more builders together with the typical additive used in detergent compositions.

Typical levels of the catalyst of the present invention in fully formulated compositions will range from 0.00005 to 2 wt.% with 0.005 to 1 wt.% being particularly preferred and 0.05 to 0.5 wt.% being most particularly preferred. Typical levels of peroxygen source in fully formulated composition will range from 0.05 to 55 wt. % with 1 to 40 wt. % being particularly preferred and 5 to 25 wt. % being most particularly preferred. Preferred peroxygen sources include percarbonate and perborate.

EXAMPLES

In order that the invention may be further and better understood it will be described in detail with reference to following non-limiting examples.

Example 1

Preparation of 2-Methyl 2-Phthalimidopropanoic Acid

Phthalic anhydride (1 Kg, 4.84 mol) and 2-aminoisobutyric hacid (500 g, 6.75 mol) were pre-mixed and heated to 190° C. with stirring. Once molten, the reaction was held at this temperature until no further water was expelled, approximately 4 hours. The reaction mixture was poured into large crystallising dishes and, whilst still hot, neutralised with 10% aqueous sodium bicarbonate solution (12.5 L). The mixture was then filtered to remove any insolubles. The filtrate was acidified with concentrated hydrochloric acid until a thick white precipitate was observed. The precipitate was filtered and washed with water to remove remaining hydrochloric acid from the precipitate. The precipitate was dried under vacuum to yield the title compound as a white powder (974 g, 86%).

$^1$H NMR (500 MHz, d$^6$ acetone) 7.84 (m, 4H), 1.83 (s, 6H); $^{13}$C NMR (125 MHz) 24.87, 60.87, 123.64, 132.73, 135.19, 168.92, 174.26.

Example 2

Preparation of 2-Methyl-2-Phthalimidopropanoyl Chloride

Thionyl chloride (750 ml, 10.28 mol) was added to 2-methyl-2-phthalimidopropanoic acid (385 g, 1.65 mol) and the mixture refluxed under nitrogen for 3 hours. Excess thionyl chloride was removed under reduced pressure to yield a solid. The solid was washed with diethyl ether (2×250 ml) to yield the title compound as a white crystalline solid (408.2 g, 98%).

$^1$H NMR (500 MHz, d$^6$ acetone) 7.92 (m, 4H), 1.95 (s, 6H); $^{13}$C NMR (125 MHz) 24.32, 68.41, 124.20, 132.45, 135.78, 168.48, 175.37.

Example 3

Preparation of N,N'-1,2-Phenylenebis[2-Methyl-2-Phthalimidopropanamide]

A solution of o-phenylene diamine (34.4 g, 0.32 mol) and triethylamine (75 ml) in THF (1 L) was added drop-wise to a stirred solution of 2-methyl-2-phthalimidopropanoyl chloride (160 g, 0.63 mol) in THF (1.5 L) at a temperature of 0° C. After addition the reaction was warmed to room temperature and stirred for a further 12 hours and then refluxed for a further 2 hours. The reaction mixture was cooled in ice, filtered and the THF removed under reduced pressure. The resultant white solid was dissolved in dichloromethane (1.5 L) and washed with 1 M hydrochloric acid (3×1 L) followed by washing with a 5% sodium bicarbonate solution. The dichloromethane extract was dried (MgSO$_4$), filtered and stripped of solvent under reduced pressure to yield the title compound (149.72 g, 87%).

$^1$H nmr (500 MHz, d$^6$ DMSO) 9.41 (s, 2H), 7.83 (d,d, 4H, $^3$J=5.45 Hz, $^4$J=3.04 Hz), 7.76 (d,d, 4H, $^3$J =5.45 Hz, $^4$J=3.04 Hz), 7.51 (m, 2H), 7.17 (m, 2H), 1.73 (s, 12H); $^{13}$C nmr (125 MHz) 24.70, 61.44, 123.21, 124.60, 125.46, 130.85, 132.00, 134.82, 168.66, 171.99.

Example 4

Preparation of N,N'-1,2-Phenylenebis[2-Methyl-2-Methylpropanamide]

A stirred suspension of the protected diamide diamine (N,N'-1,2-phenylenebis [2-methyl-2-phthalimidopropanamide] (141 g, 0.26 mol) in ethanol (3 L) was refluxed and treated with hydrazine (33.7 mL, 0.69 mol). The suspension dissolved after a few minutes and the reaction mixture refluxed for a 15 hours during which a white precipitate was formed. The reaction was cooled to room temperature and the ethanol was removed under reduced pressure to yield a solid. The solid was dissolved in 2 M hydrochloric acid (8.812 L) and heated at 80° C. for an hour and then cooled to room temperature. The reaction mixture was then filtered and the filtered liquid adjusted to pH 13 with a concentrated sodium hydroxide solution to yield a deep yellow colour solution. The deep yellow colour solution was extracted with dichloromethane (3×2 L), and the combined extracts dried (MgSO$_4$). Removal of solvent under reduced pressure gave an off white solid which was washed with ether (1 L) to yield the title compound as a white solid (69.2 g, 95%).

$^1$H nmr (500 MHz, d$^6$ DMSO) 7.66 (m, 2H), 7.2 (m, 2H), 4.75 (brs), 1.36 (s, 12H); $^{13}$C nmr (125 MHz) 29.03, 55.27, 124.41, 125.15, 131.32, 177.09.

Example 5

Preparation of 3,4,8,9-Tetrahydro -3,3,6,6,9,9-Hexamethyl-1H-1,4,8,11-Benzotetraazocyclotridecane-2, 5,7,10 (6H,11H) tetrone.

The following reaction was conducted under nitrogen with vigorous stirring of the reaction mixture. Individual solutions of dimethylmalonyl chloride (18.2 g) in 1L THF and a mixture of N,N'-1,2-phenylenebis[2-methyl-2-methylpropanamide] (30g, 0.11 mol) and triethylamine (31 mL) in THF (1L) were added in a controlled manner over 10 hours to THF (750 mL) whilst maintaining the reaction mixture at 0° C. During the reaction a precipitate was formed and the reaction mixture warmed to room temperature overnight. The reaction mixture was filtered, the precipitate washed with water (4×500 mL) and dried under reduced pressure to yield the title compound (40.3 g, 100%)

$^1$H nmr (500 MHz, d$^6$ DMSO) 8.35 (brs, 2H), 7.74 (brs, 2H), 7.47 (m, 2H), 7.16 (m, 2H), 1.47 (s, 12H), 1.45 (s, 6H); $^{13}$C nmr (125 MHz) 22.70, 25.48, 51.05, 125.12, 125.58, 130.54, 172.45, 173.23.

Example 6

Metallation of 3,4,8,9-Tetrahydro-3,3,6,6,9,9-Hexamethyl-1H-1,4,8,11-Benzotetraazocyclotridecane-2, 5,7,10 (6H, 11H) Tetrone.

A stirred suspension of 3,4,8,9-tetrahydro-3,3,6,6,9,9-hexamethyl -1H-1,4,8,11-benzotetraazocyclotridecane-2,5, 7,10 (6H,11H) tetrone (5 g) in THF (1 L) under a nitrogen atmosphere was heated to 40° C. The heated suspension was then treated with 31 mL butyl lithium causing the suspension to dissolve; 30 minutes after the treatment iron (II) chloride was added. After 36 hours the reaction mixture was cooled and filtered to provide a solid. The solid was dissolved in water (1 L) yielding a solution of pH 12 which was stirred and treated with a lithium hydroxide solution (1.5 mL) followed by addition of concentrated hydrochloric acid until the pH of the solution was 5 (colour change from brown to red/orange). The pH of the solution was then adjusted to pH 7 by addition of a lithium hydroxide solution and the solvent removed under reduced pressure to yield a sticky orange solid. The sticky orange solid was washed with methanol to provide a powder The powder was purified by dissolution in ethanol and elution through a Florisil™ column with acetonitrile to yield the title compound.

Wash Examples

In the Following wash Examples 7 to 9 a 'base' colour washing powder with approximately the following composition was used (all percentages by weight). This 'base' differs slightly from commercial powders in that it does not contain colour care components. Otherwise, the composition is very similar to that of products available at present in the marketplace.

| | |
|---|---|
| Sodium linear alkyl (C12) benzene sulphonate | 7.9% |
| C12–14 Nonionic 7 EO | 5.1% |
| C12–14 Nonionic 3 EO | 4.0% |
| Soap | 0.35% |
| Fatty Acid | 0.40% |
| Sodium tripolyphosphate | 30.0% |
| Sodium silicate | 7.9% |
| Sodium sulphate | 14.5% |
| Sodium hydrogen carbonate | 4.0% |
| Sodium carbonate | 8.8% |
| Minors and water | to 100% |

Minors included an antifoam agent, a soil release polymer, protease, lipolase, amylase and perfume.

Colour of test samples are expressed in terms of ΔE. For further detail of this measurement the reader is directed to "Measuring Colour" by R. W. G. Hunt, Series in Applied Science and Industrial Technology, Ellis Horwood, (1976) and in particular page 76 in which the CIELAB colour difference equation is given.

The following experiments were performed in what is known as "over the side experiments"; the components as detailed were added separately via the draw of the washing machine to the wash.

Example 7

Washing Experiment

The Base colour washing powder (105 g) was placed in the drawer of a Miele Novotronic (RTM) European-type horizontal-axis washing machine and the machine used to wash a 2.566 kg wash load. The load comprised 1250 g non-mercerised white cotton sheeting, 1250 g 50:50 white polycotton sheeting, and 5×900 cm² green cloth, 'direct green 26' at 5%, unfixed, weighing 66 g. The wash was conducted using the machines 40° C. program and 26° French hard water.

After the wash the cloths were tumble dried and examined. Visual examination revealed that both the white cotton and poly-cotton sheeting had both become green due to pick up of dye lost from the direct green cloth. Measurement of the CIELAB ΔE value of the cotton cloth compared to the original white gave a value of 10.5.

The experiment was repeated with fresh cloth but in the presence of 0.035 g of the catalyst prepared in example 6 and 3.63 g of a 35% solution of $H_2O_2$ was added. The CIELAB ΔE value of the cotton cloth compared to the original white was 2.4. Visual examination showed that the amount of green dye transferred to the white cloths had been significantly reduced.

Example 8

Washing Experiment

The protocol of example 7 was followed except the wash load consisted of 2.566 kg of a soiled load (dirty tea towels, pillow cases and towels, all 100% white cotton; 10 400 cm² clean white cotton monitor cloths; 5 900 cm² green cloth, dyed with direct green 26 at 5%, unfixed.

After the washing and drying the white cotton cloths showed transference of the green dye on visual inspection. The CIELAB ΔE value of the cotton monitor cloth compared to the original white was 7.4

The experiment was repeated with fresh cloth but with the levels of catalyst prepared in example 6 and levels of an aqueous 35% solution of $H_2O_2$ added as shown in Table 1 below. The average CIELAB ΔE value of the cotton monitor cloths at the various levels of catalyst and peroxide are given in Table 1 below. It can be seen that catalyst has reduced dye transfer when present.

TABLE 1

| Added catalyst in grams | Added $H_2O_2$ (35%) in grams | Measured ΔE |
|---|---|---|
| 0 | 0 | 7.4 |
| 0.035 | 3.63 | 4.0 |
| 0.035 | 14.57 | 4.4 |
| 0.070 | 14.52 | 3.7 |

Example 9

Washing Experiment

The protocol of example 7 was repeated, except the load consisted of 1.5 kg of white Terry towelling, 600 g cotton sheeting, 400 g of 1% unfixed Direct Black 22 cotton cloth.

When washed without the catalyst being present the white cloth became visibly grey, and the CIELAB ΔE value of the cotton sheeting was 14.4 compared to the original. When the catalyst was added at levels of 0.0035 g with 0.36 g of a 35% solution of $H_2O_2$, the CIELAB ΔE value of the cotton sheeting was 6.5 compared to the original. It can again be seen that dye transfer had been considerably reduced in the presence of the catalyst.

What is claimed is:

1. A method for the synthesis of a ligand having the structure:

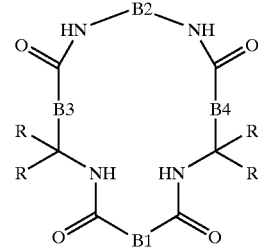

wherein:
$B_1$, $B_3$ and $B_4$ each represent a bridging group having zero, one two or three carbon containing nodes for substitution, and $B_2$ represents a bridging group having at least one carbon containing node for substitution, each said node containing a C(R), C($R_1$) ($R_2$) or C(R)$_2$,
each R substituent is the same is the same or different from the remaining R substituents and
  (i) is selected from the group consisting of alkyl, alkenyl, cycloalkyl, cycloalkenyl, aryl, alkynyl, alkylaryl, halogen, alkoxy, phenoxy and combinations thereof, or
  (ii) form a substituted or unsubstituted benzene ring of which two carbons on the ring form nodes in the B-unit,
said method comprising the steps listed below in the order given
  a) protecting the amino group of an amino acid comprising HOOC—$B_3$—CRR—$NH_2$ and/or HOOC—$B_4$—CRR—$NH_2$,
  b) activating the carbonyl group of said amino acid,
  c) reacting the carbonyl-activated amino acid with a diamine $H_2N$—$B_2$—$NH_2$ to form a diamide diamine,
  d) deprotecting said protected amino groups, and,
  e) reacting the de-protected diamide diamine with an activated di-carbonyl compound to form a tetra-amine macrocycle.

2. A method according to claim 1, wherein R=methyl.

3. A method according to claim 1, wherein B3 and B4 are absent.

4. A method according to claim 1, wherein B3=B4.

5. The method according to claim 1 wherein activating the carbonyl group of said amino acid comprises:
  adding a thionyl halide to the amino acid;
  refluxing under nitrogen for three hours to form carbonyl-activated amino acid;
  removing any excess thionyl halide under reduced pressure to yield a solid carbonyl-activated amino; and
  washing the solid.

6. The method according to claim 5 wherein the thionyl halide is thionyl chloride.

7. The method according to claim 1 wherein the amino group is protected by mixing with phthalic anhydride and heating to a temperature sufficient to render the mixture molten, maintaining the temperature until no further water is expelled from the mixture, neutralizing the hot mixture to from a precipitate, and filtering the precipitate.

8. The method according to claim 1 wherein reacting the carbonyl-activated amino acid with a diamine comprises:

adding the diamine drop wise to the carbonyl-activated amino acid in the presence of a solvent at a temperature of 0° C.

9. The method according to claim 8 further comprising:

following the addition of the diamine, warning the diamine amino acid mixture to room temperature while stirring for twelve hours;
refluxing the mixture;
cooling removing the solvent under pressure
washing the resultant precipitate 10. The method according to claim 1 wherein reacting the de-protected diamide diamine with the activated di-carbonyl compound comprises:

adding a dicarbonyl compound to a dilute mixture of the de-protected diamide diamine and a solvent in a controlled manner at 0° C. over ten hours while stirring;
warming to room temperature; and,
filtering a precipitate;
washing and drying the precipitate to yield the tetra-amine macrocycle.

11. The method according to claim 10 wherein the dicarbonyl compound is selected from malanates and oxalates. di-carbonyl compound compri

* * * * *

UNITED STATES PATENT AND TRADEMARK OFFICE
CERTIFICATE OF CORRECTION

PATENT NO. : 6,992,184 B2  
APPLICATION NO. : 10/362088  
DATED : January 31, 2006  
INVENTOR(S) : Carina et al.

It is certified that error appears in the above-identified patent and that said Letters Patent is hereby corrected as shown below:

On the Title Page, Item [56]:
In Other Publications:
Under Al-Hassan: delete "Al-Hassan. S.S." and substitute therefor --Al-Hassan, S.S.--
Under Greene: delete "Protactive" and substitute therefor --Protective--
Under Larock: delete "$2^{2nd}$" and substitute therefor --$2^{nd}$--

In Background of Invention:
Col. 1, Ln. 48: delete "a alpha-amino" and substitute therefor --an alpha-amino
Col. 2, Ln. 45: delete "is the same" (second occurrence)
Col. 3, Ln. 40: delete "is the same" (second occurrence)
Col. 4, Ln. 23: delete "selected from" (second occurrence)
Col. 6, Ln. 41: delete "hacid" and substitute therefor --acid--

In the Claims:
Col. 10, Ln. 30, in Claim 1: delete "is the same" (second occurrence)
Col. 11, Ln. 2, in Claim 9 delete "warning" and substitute therefor --warming--
Col. 11, Ln. 14, in Claim 9 delete "refluxing the mixture; cooling removing the solvent under pressure washing the resultant precipitate" and substitute therefor --refluxing; cooling the mixture; removing the solvent under pressure; and washing the resultant precipitate.--
Col. 12, Ln. 13, in Claim 11 delete "from malanates and oxalates. Di carbonyl compound compri." and substitute therefor --from malonates and oxalates.--

Signed and Sealed this

Twenty-eighth Day of November, 2006

JON W. DUDAS  
*Director of the United States Patent and Trademark Office*